United States Patent
Andersson et al.

(10) Patent No.: US 7,214,850 B2
(45) Date of Patent: May 8, 2007

(54) TRANSGENIC MOUSE EXPRESSING PRKAG3

(75) Inventors: Leif Andersson, Uppsala (SE); Stefan Marklund, Uppsala (SE)

(73) Assignee: Arexis AB, Gothenburg (SE)

( * ) Notice: Subject to any disclaimer, the term of this patent is extended or adjusted under 35 U.S.C. 154(b) by 0 days.

(21) Appl. No.: 10/503,175

(22) PCT Filed: Jan. 31, 2003

(86) PCT No.: PCT/IB03/00912

§ 371 (c)(1),
(2), (4) Date: Feb. 15, 2005

(87) PCT Pub. No.: WO03/063586

PCT Pub. Date: Aug. 7, 2003

(65) Prior Publication Data

US 2005/0172348 A1    Aug. 4, 2005

Related U.S. Application Data

(60) Provisional application No. 60/353,430, filed on Feb. 1, 2002.

(51) Int. Cl.
*A01K 67/027* (2006.01)
*A01K 67/00* (2006.01)
*G01N 33/00* (2006.01)
*C12N 15/00* (2006.01)

(52) U.S. Cl. .................... 800/18; 800/3; 800/8; 800/25

(58) Field of Classification Search .................... 800/3, 800/14–18, 25, 8
See application file for complete search history.

(56) References Cited

U.S. PATENT DOCUMENTS

| 4,873,191 A | 10/1989 | Wagner et al. |
| 4,946,778 A | 8/1990 | Ladner et al. |
| 5,846,720 A | 12/1998 | Foulkes et al. |

FOREIGN PATENT DOCUMENTS

| WO | WO 97/25341 | 7/1997 |
| WO | WO 01/20003 | 3/2001 |
| WO | WO 01/77305 | 10/2001 |

OTHER PUBLICATIONS

Kappel et al. Current Biology, 1992, 3: 548-553.*
Mullins et al. Hypertension, 1993, 22: 630-633.*
Houdebine et al. Journal of Biotechnology, 1994, 34: 269-287.*
Wall R.J. Theriogenology, 1996, 45: 57-68.*
Mullins et al. Journal of Clinical Investigation, 1996, 98(11): S37-S40.*
Cameron E. Molecular Biology, 1997, 7: 253-265.*
Sigmund C. Arterioscler. Thromb. Vasc. Biol., 2000, 20: 1425-1429.*
Niemann H. Transgenic Research, 1998, 7: 73-75.*
Schoonjans et al. Stem Cells, 2003, 21: 90-97.*
Hochepied et al. Stem Cells, 2004, 22: 441-447.*
Rülicke et al. Germ Line Transformation of Mammals by Pronuclear Microinjection. Experimental Physiol. 2000, vol. 85, No. 6, 589-601.*
Wolf et al. Transgenic Technology in Farm Animals—Progress and Perspectives. Experimental Physiol. vol. 85, No. 6, pp. 615-625.*
Smith. Gene Transfer in Higher Animals: Theoretical Considerations and Key Concepts. J. Biotech. 2002, vol. 99, pp. 1-22.*
GenBank Accession No. AB022017 dated Jan. 8, 1999, 2 pages.
GenBank Accession No. AAH48980 dated Apr. 22, 2003, 2 pages.
GenBank Accession No. AC009974 dated Feb. 11, 2004, 120 pages.
GenBank Accession No. AF214519 dated Jun. 3, 2000, 2 pages.
GenBank Accession No. AF249977 dated Jun. 28, 2001, 1 page.
Cheung et al., "Characterization of AMP-activated protein kinase γ-subunit isoforms and their role in AMP binding," *Biochem. J.*, 2000, 346:659-669.
Collins, "Generation and initial analysis of more than 15,000 full-length human and mouse cDNA sequences," *Proc. Natl. Acad. Sci. USA*, 2002, 99(26):16899-16903.
Cote et al., "Generation of human monoclonal antibodies reactive with cellular antigens," *Proc. Natl. Acad. Sci. USA*, 1983, 80:2026-2030.
Davies et al., "Tissue distribution of the AMP-activated protein kinase, and lack of activation by cyclic-AMP-dependent protein kinase, studied using a specific and sensitive peptide assay," *Eur. J. Biochem.*, 1989, 186:123-128.
Engh and Bossemeyer, "The Protein Kinase Activity Modulation Sites: Mechanisms for Cellular Regulation—Targets for Therapeutic Intervention," *Advan. Enzyme Regul.*, 2001, 41:121-149.
Foretz et al., "AMP-activated Protein Kinase Inhibits the Glucose-activated Expression of Fatty Acid Synthase Gene in Rat Hepatocytes," *J. Biol. Chem.*, 1998, 273(24):14767-14771.
Goodyear, "AMP-Activated Protein Kinase: A Critical Signaling Intermediary for Exercise-Stimulated Glucose Transport?" *Exerc. Sport Sci. Rev.*, 2000, 28:113-116.
Gros et al., "Insulin production by engineered muscle cells," *Hum. Gene Ther.*, 1999, 10(7):1207-1217.
Hardie and Carling, "The AMP-activated protein kinase. Fuel gauge of the mammalian cell?" *Eur. J. Biochem.*, 1997, 246:259-273.
Hardie et al., "The AMP-Activated/SNF1 Protein Kinase Subfamily: Metabolic Sensors of the Eukaryotic Cell?" *Annu. Rev. Biochem.*, 1998; 67:821-855.
Hardie and Hawley, "AMP-activated protein kinase: the energy charge hypothesis revisited," *BioEssays*, 2001, 23:1112-1119.

(Continued)

*Primary Examiner*—Deborah Crouch
(74) *Attorney, Agent, or Firm*—Fish & Richardson P.C.

(57) ABSTRACT

Transgenic non-human animals that express the γ3 subunit of PRKAG are described, as well as methods of using the transgenic non-human animals as models for improving treatment, prevention, or diagnosis of diseases related to energy metabolism, including obesity, dyslipidemia, insulin resistance syndrome, and type 2 diabetes.

14 Claims, 3 Drawing Sheets

OTHER PUBLICATIONS

Hayashi et al., "Evidence for 5' AMP-Activated Protein Kinase Mediation of the Effect of Muscle Contraction on Glucose Transport," *Diabetes*, 1998, 47:1369-1373.

Holmes et al., "Chronic activation of 5'-AMP-activated protein kinase increases GLUT-4, hexokinase, and glycogen in muscle," *J. Appl. Physiol.*, 1999, 87(5):1990-1995.

Huse et al., "Generation of a Large Combinatorial Library of the Immunoglobulin Repertoire in Phage Lambda," *Science*, 1989, 246:1275-1281.

Kemp et al., "Dealing with energy demand: the AMP-activated protein kinase," *Trends Biochem. Sci.*, 1999, 24(1):22-25.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Lo, "Transformation by Iontophoretic Microinjection of DNA: Multiple Integrations Without Tandem Insertions," *Mol. Cell. Biol.*, 1983, 3:1803.

Lochhead et al., "5-Aminoimidazole-4-Carboxamide Riboside Mimics the Effects of Insulin on the Expression of the 2 Key Gluconeogenic Genes PEPCK and Glucose-6-Phosphatase," *Diabetes*, 2000, 49:896-903.

Michell et al., "Isoform-specific Purification and Substrate Specificity of the 5'-AMP-activated Protein Kinase," *J. Biol. Chem.*, 1996, 271(45):28445-28450.

Merrill et al., "AICA riboside increases AMP-activated protein kinase, fatty acid oxidation, and glucose uptake in rat muscle," *Am. J. Physiol.*, 1997, 273:E1107-E1112.

Milan et al., "A Mutation in *PRKAG3* Associated with Excess Glycogen Content in Pig Skeletal Muscle," *Science*, 2000, 288:1248-1251.

Thompson et al., "Germ Line Transmission and Expression of a Corrected HPRT Gene Produced by Gene Targeting in Embryonic Stem Cells," *Cell*, 1989, 56:313-321.

Van der Putten et al., "Efficient insertion of genes into the mouse germ line via retroviral vectors," *Proc. Natl. Acad. Sci. USA*, 1985, 82:6148-6152.

Wakayama et al., "Full-term development of mice from enucleated oocytes injected with cumulus cell nuclei," *Nature*, 1998, 394:369-374.

Wilmut et al., "Viable offspring derived from fetal and adult mammalian cells," *Nature*, 1997, 385(6619):810-813.

Winder and Hardie, "AMP-activated protein kinase, a metabolic master switch: possible roles in Type 2 diabetes," *Am. J. Physiol.*, 1999, 277:E1-E10.

Zhou et al., "Role of AMP-activated protein kinase in mechanism of metformin action," *J. Clin. Invest.*, 2001, 108(8):1167-1174.

* cited by examiner

Endogenic *Prkag3*

Transgenic *Prkag3*

TRANSGENIC MOUSE EXPRESSING PRKAG3

CROSS-REFERENCE TO RELATED APPLICATIONS

This application is a National Stage application under 35 U.S.C. § 371 and claims benefit under 35 U.S.C. § 119(a) of International Application No. PCT/IB03/00912 having an International Filing Date of Jan. 31, 2003, which claims the benefit of priority of U.S. Provisional Application Ser. No. 60/353,430 having a filing date of Feb. 1, 2002.

TECHNICAL FIELD

This invention relates to transgenic non-human animals expressing an AMP-activated protein kinase (AMPK) γ3 subunit, their use as models of studying human disease, and to methods of using these models for identifying compounds and compositions effective for the treatment of disease. In particular, the invention relates to transgenic non-human animals expressing the Prkag3 gene in skeletal muscle.

BACKGROUND

AMPK has a key role in regulating the energy metabolism in eukaryotic cells and is homologous to the SNF1 kinase in yeast (Hardie D. G., et al., 1998, *Annu. Rev. Biochem.* 67:821; Kemp B. E., et al., 1999, *Trends. Biochem. Sci.* 24(1):22–5). AMPK is composed of three subunits: the catalytic α-subunit and the two regulatory subunits β and γ. AMPK is activated by an increase in the ratio of AMP to ATP (AMP:ATP). Activated AMPK turns on ATP-producing pathways and inhibits ATP-consuming pathways. AMPK also can inactivate glycogen synthase, the key regulatory enzyme of glycogen synthesis, by phosphorylation (Hardie et al., 1998, supra). Several isoforms of the three different AMPK subunits are present in mammals. In humans, Prkaa1 and Prkaa2 encode the α1 and α2 subunits, Prkab1 and Prkab2 encode the β1 and β2 subunits, and Prkag1, Prkag2 and Prkag3 encode the γ1, γ2 and γ3 subunits, respectively.

Milan D., et al. (2001, *Science,* 288:1248–5) identified the nonconservative substitution of a glutamine for an Arginine (R225Q) in the Hampshire pig Prkag3 gene responsible for the dominant RN-phenotype (high glycogen content in skeletal muscle). Loss-of-function mutations in the homologous gene in yeast (SNF4) cause defects in glucose metabolism, including glycogen storage. Milan et al. further found that the expression of the Prkag3 gene is muscle-specific and that the AMPK activity in muscle extracts was about 3 times higher in normal rn+ pigs than in RN− pigs, both in the presence and absence of AMP. The distinct phenotype of the RN-mutation indicates that Prkag3 plays a key role in the regulation of energy metabolism in skeletal muscle.

AMPK is recognized as a major regulator of lipid biosynthetic pathways due to its role in the phosphorylation and inactivation of key enzymes such as acetyl-CoA carboxylase (ACC) (Hardie D. G., and Carling D., 1997, *Eur. J. Biochem.* 246:259–273). More recent data strongly suggest that AMPK has a wider role in metabolic regulation (Winder W. W., and Hardie D. G., 1999, *Am. J. Physiol.,* 277:E1–E10): this includes fatty acid oxidation, muscle glucose uptake (Hayashi T., et al., 1998, *Diabetes,* 47:1369–1373; Merrill G. F., et al., *Am. J. Physiol.* 273:E1107–E1112; Goodyear L. J., 2000, *Exerc. Sport Sci. Rev.,* 28:113–116), expression of cAMP-stimulated gluconeogenic genes such as PEPCK and G6Pase (Lochhead P. A., et al., 2000, *Diabetes,* 49:896–903), and glucose-stimulated genes associated with hepatic lipogenesis, including fatty acid synthase (FAS), Spot-14 (S14), and L-type pyruvate kinase (Foretz M., et al., 1998, *J. Biol. Chem.,* 273:14767–14771). Chronic activation of AMPK may also induce the expression of muscle hexokinase and glucose transporters (Glut4), mimicking the effects of extensive exercise training (Holmes B. F., et al., 1999, *J. Appl. Physiol.* 87:1990–1995). Thus, it has been predicted that AMPK activation would be a good approach to treat type 2 diabetes (Winder et al., supra).

Zhou G, et al. (2001, *J. Clin. Invest.,* 108:1167–1174) provided evidence that the elusive target of metformin's (a widely used drug for treatment of type 2 diabetes) actions is activated AMPK. In studies performed in isolated hepatocytes and rat skeletal muscles, metformin leads to AMPK activation, accompanied by an inhibition of lipogenesis (due to inactivation of acetyl-CoA carboxylase and suppression of lipogenic enzyme expression), suppression of the expression of SREBP-1 (a central lipogenic transcription factor), and a modest stimulation of skeletal muscle glucose uptake. Similar hepatic effects are seen in metformin-treated rats. Based on the use of a newly discovered AMPK inhibitor, their data suggest that the ability of metformin to suppress glucose production in hepatocytes requires AMPK activation.

SUMMARY

The invention is based on transgenic non-human animals expressing the AMPK γ3 subunit and their use as a model for diseases relating to energy metabolism, including obesity, dyslipidemia, insulin resistance syndrome, and type 2 diabetes. Such models can be used to improve diagnosis of diseases relating to energy metabolism as well as identifying and testing pharmaceutical compositions for better treatment and prevention of diseases relating to energy metabolism.

In one aspect, the invention features a transgenic non-human animal having integrated within its genome a nucleic acid encoding an AMP-activated protein kinase γ3 subunit or a variant thereof, wherein the nucleic acid is operably linked to a regulatory element. The nucleic acid can include a nucleotide sequence encoding a polypeptide having at least 75% sequence identity to the amino acid sequence set forth in SEQ ID NO:2. The nucleic acid can encode a polypeptide having an amino acid sequence selected from the group consisting of: (a) the amino acid sequence set forth in SEQ ID NO:2, (b) an R225Q variant of the amino acid sequence set forth in SEQ ID NO:2; (c) the amino acid sequence set forth in SEQ ID NO:4; and (d) an R225Q variant of the amino acid sequence set forth in SEQ ID NO:4. The nucleic acid can include a nucleotide sequence selected from the group consisting of (a) the nucleotide sequence set forth in SEQ ID NO:1; (b) a codon 225 variant of the nucleotide sequence set forth in SEQ ID NO:1; (c) the nucleotide sequence set forth in SEQ ID NO:3, (d) a codon 225 variant of the nucleotide sequence set forth in SEQ ID NO:3; (e) the nucleotide sequence set forth in SEQ ID NO:5; and (f) a nucleotide sequence corresponding to the mouse Prkag3 gene. The regulatory element can be a muscle specific regulatory element such as a myosin light chain promoter, a skeletal alpha actin promoter, a creatine kinase promoter, or an aldolase A promoter. The transgenic non-human animal can be selected from the group consisting of mice, rats, rabbits, cats, dogs, and pigs. Transgenic mice and pigs are particularly useful. Transgenic non-human animals can have an elevated glycogen content in skeletal muscle.

In another aspect, the invention features a transgenic non-human animal having a transgene integrated within its genome. The transgene includes a nucleotide sequence which hybridizes under stringent hybridization conditions (e.g., highly stringent) with a nucleic acid having a nucleotide sequence complementary to the nucleotide sequence of SEQ ID NO:1 or a portion thereof, wherein the transgene acid is operably linked to a promoter that drives expression in skeletal muscle. The transgenic non-human animal can be selected from the group consisting of mice, rats, rabbits, cats, dogs, and pigs.

The invention also features an expression construct. The expression construct includes a regulatory element operably linked to a nucleotide sequence encoding a polypeptide having at least 75% sequence identity to the amino acid sequence shown in SEQ ID NO:2 or to a portion thereof; where the regulatory element is capable of mediating expression in skeletal muscle. The regulatory element can be muscle-specific regulatory element such as myosin light chain promoter, a myosin heavy chain promoter, a skeletal alpha actin promoter, a creatine kinase promoter, or an aldolase A promoter.

In yet another aspect, the invention features an expression construct that includes a regulatory element operably linked to a nucleotide sequence having at least 75% sequence identity to the nucleotide sequence shown in SEQ ID NO:1; where the regulatory element is capable of mediating expression in skeletal muscle. The regulatory element can be a muscle specific regulatory element as described above.

The invention also features a method for making a transgenic non-human animal having integrated within its genome a nucleic acid encoding an AMP activated protein kinase γ3 subunit or a variant thereof The nucleic acid is linked to a regulatory element that drives expression in skeletal muscle. The method includes introducing an expression construct described above into an ovum, an embryo, or embryonic stem cells of a non-human animal. The expression construct can be microinjected into the ovum or embryo of the non-human animal or into embryonic stem cells of the non-human animal. The expression construct can be electroporated into the embryonic stem cells.

In yet another aspect, the invention features a method of identifying a compound or composition effective for the treatment or prevention of a disease related to energy metabolism. The method includes (a) administering a test compound or test composition to a transgenic non-human animal described above; and (b) evaluating the effect of the test compound or test composition on the energy metabolism on the transgenic non-human animal; wherein the test compound or test composition is identified as effective for the treatment or prevention of the disease related to energy metabolism if energy metabolism is altered.

The invention also features a method of identifying a compound or composition effective for the treatment or prevention of diseases related to energy metabolism. The method includes (a) contacting a test compound or test composition with an organ, a tissue or cells derived from a transgenic non-human animal described above; and (b) evaluating the effect of the test compound or test composition on the energy metabolism on the organ, tissue or cells; wherein the test compound or test composition is identified as effective for the treatment or prevention of diseases related to energy metabolism if energy metabolism is altered. The tissue can be skeletal muscle. The cells can be muscle cells.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
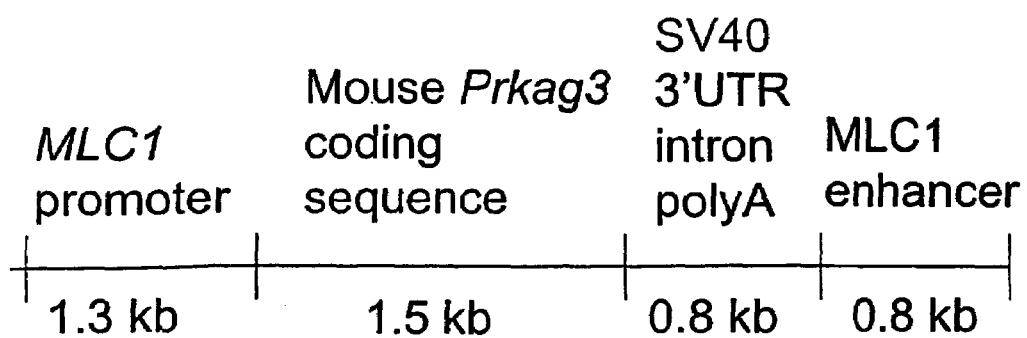
FIG. 1 is a schematic of the linearized construct used for microinjection into mouse oocytes. Microinjection was done with two constructs separately, one construct included the wild-type mouse Prkag3 cDNA and the other construct included the mouse Prkag3 cDNA encoding the R225Q mutant.

The invention relates to transgenic non-human animals that express the AMPK γ3 subunit and methods of using the animals for the development of drugs for the treatment or prevention of diseases related to energy metabolism, such as obesity, dyslipidemia, insulin resistance syndrome, and type 2 diabetes. Without being bound by a particular mechanism, modulation of the amount or activity of the γ3 subunit of AMPK, a major cellular regulator of lipid and glucose metabolism, may be beneficial in the treatment of such energy metabolism diseases. An increase in overall activity of AMPK in muscle can increase levels of glycogen, which is coupled to increased glucose uptake and lowered blood glucose levels.

As used herein, "transgenic non-human animal" includes the founder transgenic non-human animals and progeny of the founders, as well as cells and tissues from such animals. Transgenic non-human animals can be farm animals such as pigs, goats, sheep, cows, horses, and rabbits, rodents such as rats, guinea pigs, and mice, and non-human primates such as baboons, monkeys, and chimpanzees. Transgenic pigs and mice are particularly useful.

A transgenic non-human animal of the invention contains a nucleic acid encoding an exogenous AMPK γ3 subunit (e.g., a human, mouse, or pig AMPK γ3 subunit) integrated within its genome. As used herein, the term "AMPK γ3 subunit" refers to a polypeptide having at least 200 amino acids (e.g., at least 300 or 400 amino acids) of the full-length polypeptide. In some embodiments, the AMPK γ3 subunit is full-length. The AMPK γ3 subunit can be wild-type or can be a variant (e.g., the R225Q variant). The cDNA encoding the human γ3 subunit has been cloned and characterized (WO 01/20003; Milan et al., 2001, supra; GenBank Accession Nos. AF214519 and AF249977; Cheung P. C., et al., 2000, *Biochem J.*, 346: 659–69). Genetic variants of the human Prkag3 gene encoding the AMPK γ3 subunit have been identified (WO 01/77305). The mouse sequence encoding the AMPK γ3 subunit is provided in SEQ ID NO:3.

In some embodiments, the exogenous nucleic acid can encode a polypeptide having at least 75% (e.g., at least 80%, 85%, 90%, 95%, 98%, or 99%) sequence identity to the amino acid sequence shown in SEQ ID NO:2 or SEQ ID NO:4, or to a fragment of SEQ ID NO:2 or SEQ ID NO:4 at least 200 amino acids in length. The nucleic acid molecule can encode the amino acid sequence of SEQ ID NO:2 or SEQ ID NO:4, an R225Q variant of SEQ ID NO:2 or SEQ ID NO:4, or fragments of such polypeptides that are at least 200 amino acids in length.

In other embodiments, the exogenous nucleic acid includes a nucleotide sequence having at least 75% sequence identity (e.g., at least 80%, 85%, 90%, 95%, 98%, or 99%) to the nucleotide sequence shown in SEQ ID NO:1 or SEQ ID NO:3, or to a fragment of SEQ ID NO:1 or SEQ ID NO:3 at least 600 nucleotides in length (e.g., at least 900 or 1200 nucleotides in length). In some embodiments, the nucleic acid includes the nucleotide sequence set forth in SEQ ID NO:1 or SEQ ID NO:3, a codon 225 variant (e.g., R225Q variant) of the nucleotide sequences set forth in SEQ ID NO:1 or SEQ ID NO:3, or a fragment of such nucleic acids at least 600 nucleotides in length.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (world wide web at fr.com/blast) or the U.S. government's National Center for Biotechnology Information web site (world wide web at ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q −1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 850 nucleotides from the target sequence aligned with a region of the sequence set forth in SEQ ID NO:1 where the first and last nucleotides of that 850 nucleotide region are matches, and (3) the number of matches over those 850 aligned nucleotides is 750, then the 1000 nucleotide target sequence contains a length of 850 and a percent identity over that length of 88 (i.e., 750) 850×100=88).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

It is contemplated that it may be useful to include intron sequences in a nucleic acid encoding an AMPK γ3 subunit or a variant thereof. For example, one or more of the intron sequences present in the Prkag3 gene shown in SEQ ID NO:5 can be included in the nucleic acid. It is likely that not all of the intron sequences are necessary and that intron sequences from Prkag3 from other species or intron sequences from genes coding for other protein may also be suitable and can be inserted into the nucleotide sequence coding for the γ3 subunits of AMPK in a suitable manner.

Nucleic acid useful in the invention will generally hybridize under stringent conditions with the sequence complementary to the nucleotide sequence of SEQ ID NO:1 or a fragment thereof at least 600 nucleotides in length. Thus, a transgenic non-human animal of the invention can have integrated within its genome, a nucleic acid that hybridizes with the complementary sequence to the nucleotide sequence of SEQ ID NO:1 or a part thereof under stringent hybridization conditions. Suitable nucleic acids can hybridise under highly stringent hybridization conditions. The term "stringent" when used in conjunction with hybridization conditions is as defined in the art, i.e., 15–20° C. under the melting point Tm. Preferably the conditions are highly stringent", i.e., 5–10° C. under the melting point Tm. High stringency conditions can include the use of low ionic strength buffer and a high temperature for washing, for example, 0.015 M NaCl/0.0015 M sodium citrate (0.1× SSC), 0.1% sodium dodecyl sulfate (SDS) at 65° C. Alternatively, denaturing agents such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Defining appropriate hybridization conditions is within the skill of the art. See, e.g., Molecular Cloning: A Laboratory Manual, 3rd ed., Sambrook et al. eds., Cold Spring Harbor Laboratory Press, 2001; DNA Cloning: A practical Approach, Glover & Hames eds., Oxford University Press, 1996; Nucleic Acid Hybridization: Essential techniques, Ross ed. Wiley, 1998.

In transgenic non-human animals of the invention, the nucleic acid is operably linked to a regulatory element that can promote expression in muscle. As used herein, the term "operably linked" refers to the placement of the regulatory element and nucleic acid in such a manner that the nucleic acid is transcribed. The regulatory element can be a skeletal muscle specific promoter, such as a myosin light chain promoter, a myosin heavy chain promoter, a skeletal alpha actin promoter, a creatine kinase promoter, or an aldolase A promoter.

The invention also features expression constructs suitable for generating transgenic non-human animals of the invention. The expression constructs can include a promoter capable of mediating expression in skeletal muscle operably linked to a nucleic acid encoding an AMPK γ3 subunit as described above.

Various techniques known in the art can be used to introduce expression constructs into non-human animals to produce the founder lines of the transgenic non-human animals. Such techniques include, but are not limited to, pronuclear microinjection (U.S. Pat. No. 4,873,191), retrovirus mediated gene transfer into germ lines (Van der Putten et al., *Proc. Natl. Acad. Sci. USA*, 82:6148, 1985), gene targeting into embryonic stem cells (Thompson et al., *Cell*, 56:313, 1989), electroporation of embryos (Lo, *Mol. Cell. Biol.*, 3:1803, 1983), and transformation of somatic cells in vitro followed by nuclear transplantation (Wilmut et al., *Nature*, 385(6619):810–813, 1997; and Wakayama et al., *Nature*, 394:369–374, 1998).

In a preferred embodiment, the expression construct is microinjected into an ovum or embryo of the non-human animal or into embryonic stem cells of the non-human animal.

Once transgenic non-human animals have been generated, expression of the AMPK γ3 subunit can be assessed using standard techniques. Initial screening can be accomplished by Southern blot analysis or PCR techniques to determine whether or not integration of the transgene has taken place. See, for example, sections 9.37–9.52 of Sambrook et al., 1989, "Molecular Cloning, A Laboratory Manual," second edition, Cold Spring Harbor Press, Plainview; N.Y., for a description of Southern analysis.

Expression of the nucleic acid encoding AMPK γ3 subunit in the tissues of the transgenic non-human animals can be assessed using techniques that include, but are not limited to, Northern blot analysis of tissue samples obtained from the animal, in situ hybridization analysis, and reverse-transcriptase PCR (RT-PCR).

Methods of Using Transgenic Non-Human Animals

As discussed above, transgenic non-human animals according to the invention can be used as a model for diseases related to energy metabolism, such as obesity, dyslipidemia, insulin resistance syndrome and type 2 diabetes. In particular, transgenic non-human animals of the invention can be used to identify a compound or composition effective for the treatment or prevention of diseases related to energy metabolism. Compounds or compositions can be identified by administering a test compound or composition to a transgenic non-human animal of the invention or by contacting the test compound or composition with an organ, a tissue (e.g., skeletal muscle) or cells (e.g., muscle cells) derived from the transgenic non-human animal. Effects of the test compound or composition on the energy metabolism on the transgenic non-human animal, organ, tissues or cells are evaluated. For example, glycogen content can be assessed in the transgenic non-human animals. Test compounds or compositions that alter energy metabolism can be effective for the treatment or prevention of diseases related to energy metabolism.

Test compounds can be formulated into pharmaceutical compositions by admixture with pharmaceutically acceptable non-toxic excipients or carriers and administered to transgenic non-human animals of the invention by any route of administration. For example, parenteral routes such as subcutaneous, intramuscular, intravascular, intradermal, intranasal, inhalation, intrathecal, or intraperitoneal administration, and enteral routes such as sublingual, oral, or rectal administration can be used.

The invention will be further described in the following examples, which do not limit the scope of the invention described in the claims.

EXAMPLES

Example 1

Isolation and characterization of the human Prkag3 gene: The published cDNA sequences encoding the human AMPK γ3 subunit (Genbank accession nos. AJ249977 and AF214519) (SEQ ID NO:1) were used to search the database for genomic sequences comprising the human Prkag3 gene and promoter. The human BAC clone RP11-459I19 (Genbank accession No. AC009974) was identified and found to comprise the complete Prkag3 gene (SEQ ID NO:5). The coding part of the gene contains at least 14 exons and spans more than 8 kb. The 5' end of the reported cDNA sequence (AJ249977) consists a donor-acceptor splice signal indicating the possible presence of yet another exon in the 5' end of the gene.

Example 2

Cloning and in vitro mutagenesis of the mouse Prkag3 coding sequence: Genomic mouse Prkag3 sequence was obtained by sequencing a PRKAG3-positive clone isolated from a BAC library of mouse genomic DNA. The coding sequence was deduced from this genomic sequence with presumed start and stop codons in concordance with the human cDNA sequence in GenBank AJ249977. The mouse sequence was used to design primers for RT-PCR amplification of the complete coding Prkag3 sequence from a mouse skeletal muscle poly A RNA sample (Clontech, Palo Alto, Calif.). The mouse forward 5' CACC ATG GAG CCC GAG CTG GAG CA (SEQ ID NO:7) and reverse 5' GTC TCA GGC GCT GAG GGC ATC (SEQ ID NO:8) primer sequences include the translation start and stop codons, respectively (in bold). The forward primer also includes four additional bases (in italics) at the 5' end to facilitate translation initiation. Reverse transcription was performed on 200 ng mouse skeletal muscle mRNA using the First-Strand cDNA Synthesis Kit (Amersham Pharmacia Biotech, Little Chalfont Buckinghamshire, UK) with random hexarner priming in a 15 µl reaction volume. The resulting product was used for PCR at a 1:6 dilution at standard conditions with primer annealing at 63° C. The RT-PCR product (~1.5 kbp) was gel purified and ligated into the pCRII TA TOPO cloning vector (Invitrogen, Groningen, Netherlands). Ten clones were sequenced and the consensus sequence set forth in SEQ ID NO:3 was identical to the coding Prkag3 sequence derived from the mouse BAC. A clone of this consensus sequence was selected for inclusion of the insert in the transgenic construct and for introduction of a mutation, R225Q, corresponding to the porcine RN$^-$ mutation (Milan et al., supra). The R225Q mutation was introduced by in vitro mutagenesis of the nucleotides AG to CA at positions 685–686 in the mouse sequence given in SEQ ID NO:3, which changes the codon AGG for arginine (R) to CAG for glutamine (Q). This mutagenesis was carried out using the Quikchange Site-Directed Mutagenesis Kit (Stratagene, La Jolla, Calif.) with forward and reverse primers over the GTG GCC AAC GGT GTG CAG GCA GCT CCT CTG TGG (SEQ ID NO:9) sequence (mutagenesis site in bold).

Example 3

Transgene constructs and microinjection: The wild-type and R225Q inserts in the pCRII TA TOPO cloning vector from Example 2 were removed using an Eco RI digest. These inserts then were ligated into the pMLC vector (Gros et al. 1999) kindly provided by Dr Fatima Bosch. The resulting transgene contained the complete mouse Prkag3 coding sequence (with attached Kozak element as described above) flanked by the myosin light chain 1 (MLC1) promoter on the 5' end and the SV40 untranslated region (with a small intron and a polyA site) as well as the MLC1/3 enhancer on the 3' end (FIG. 1). The MLC1 promoter is expected to direct the expression primarily to white (fast twitch) skeletal muscle fibers. This transgene was removed from the plasmid using a NotI/XhoI double digestion and gel-purified on an agarose gel, without exposure to UV light or ethidium bromide. Wild type and R225Q mutated forms of the transgene were used for microinjection into mouse oocytes (CBAxC57B1/6J) at the Mouse Camp facility at Karolinska Institute in Stockholm (world wide web at mousecamp.ki.se).

Example 4

Figure 2:
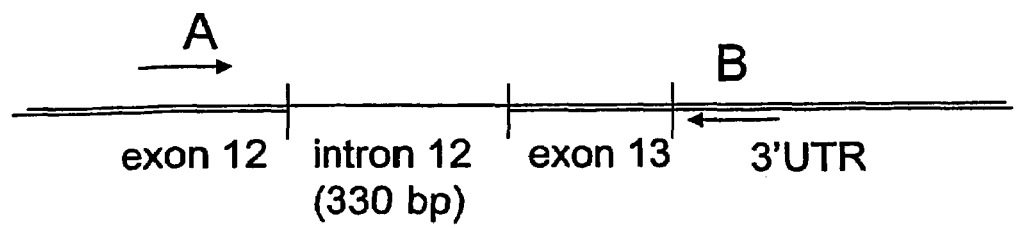
FIG. 2 is a schematic depicting the primer locations (A, B, C) and exon-intron organization in the mouse Prkag3 amplicons used for genotyping the mice (from tail-tip genomic DNA) and for skeletal muscle mRNA expression analysis by RT-PCR.
Figure 2:
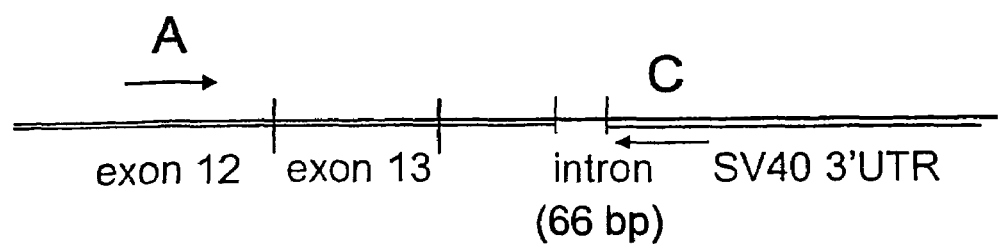

Genotyping and mRNA expression analysis: The founders were tested for transgene incorporation using a PCR test with a forward primer in Prkag3 exon 12 (5' GCT GCC CAG CAA ACC TAC AAC) (SEQ ID NO:10) and two alternative reverse primers located in the mouse Prkag3 3'UTR (5' AAG ATG GCT TGG GTG TGA GGA C) (SEQ ID NO:11); not included in the construct, and SV40 3'UTR (5' TGC TCC CAT TCA TCA GTT CCA TAG) (SEQ ID NO:12), respectively (FIG. 2). The expected PCR product sizes are shown in Table 1.

TABLE 1

Expected PCR results using the forward primer in mouse Prkag3 exon 12 and reverse primers in the 3'UTR of mouse Prkag3 and SV40, respectively.

| Gene | PCR product size (bp) | |
| --- | --- | --- |
|  | Genomic DNA | cDNA |
| Endogenic PRKAG3 | 617 | 287 |
| Transgenic PRKAG3 | 453 | 387 |

Genomic DNA was prepared from mouse tails according to a standard protocol and used in 10 µl reactions including 0.35 U AmpliTaq DNA polymerase (Perkin Elmer, Branchburg, N.J., USA), 1×PCR buffer, 1.5 mM $MgCl_2$, 0.2 MM of each dNTP, 2.5 pmol of each primer and 5% DMSO. Thermocycling was carried out using a PTC 200 instrument (MJ Research, Watertown, Mass., USA) and included 40 cycles with annealing at 58° C. for 30 s and extension at 72° C. for 1 min. The denaturation steps were at 95° C. for 1–2 min in the first two cycles, and at 94° C. for 1 min in the remaining cycles. The same set of primers was used for RT-PCR amplification of the corresponding cDNA fragments from quadriceps mRNA samples (FIG. 2, Table 1). Quadriceps mRNA was prepared using the Quickprep Micro mRNA Purification Kit (Amersham Pharmacia Biotech, Little Chalfont Buckinghamshire, UK) and used for first cDNA strand synthesis as described above. The resulting product was used for PCR at a 1:6 dilution with conditions in essence the same as for the PCR on tail genomic DNA described above. This simultaneous amplification of transgenic and endogenous Prkag3 cDNA was used for estimation of the relative transgenic/endogenous Prkag3 mRNA expression.

Example 5

Glycogen measurements: The glycogen content was measured on quadriceps samples from 18 transgenic founder females at 10–11 weeks of age. Six of these founders were from the microinjection of the Prkag3 wild type construct whereas the other 12 founders were from the microinjection of the R225Q construct.

Figure 3:
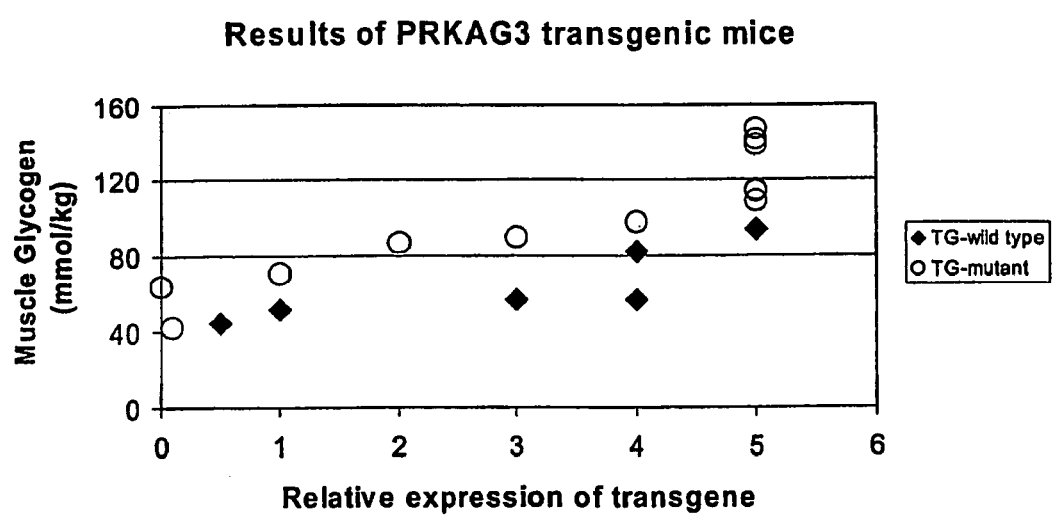
FIG. 3 is a graph depicting the glycogen content vs the relative transgenic/endogenous Prkag3 mRNA expression ratio in skeletal muscle of 18 transgenic founder females.

Among the 18 female founders tested, both constructs showed a clear association between transgenic mRNA expression and elevated glycogen levels in skeletal muscle. The most dramatic effects on glycogen levels were observed among mice with the mutated construct (FIG. 3).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse having integrated within its genome a nucleic acid encoding an AMP-activated protein kinase γ3 subunit having at least 85% sequence identity to the sequence set forth in SEQ ID NO:2, wherein said nucleic acid is operably linked to a regulatory element, and wherein said transgenic mouse has an elevated glycogen content in skeletal muscle.

2. The transgenic mouse according to claim 1, wherein said nucleic acid comprises a nucleotide sequence encoding a polypeptide having at least 90% sequence identity to the amino acid sequence set forth in SEQ ID NO:2.

3. The transgenic mouse according to claim 2, wherein said nucleic acid encodes a polypeptide having an amino acid sequence selected from the group consisting of: (a) the amino acid sequence set forth in SEQ ID NO:2, and (b) an R225Q variant of the amino acid sequence set forth in SEQ ID NO:2.

4. The transgenic mouse according to claim 1, said nucleic acid comprising a nucleotide sequence selected from the group consisting of (a) the nucleotide sequence set forth in SEQ ID NO:1; (b) a codon 225 variant of the nucleotide sequence set forth in SEQ ID NO:1; and (c) the nucleotide sequence set forth in SEQ ID NO:5.

5. The transgenic mouse according to claim 1, wherein said regulatory element is a muscle specific regulatory element.

6. The transgenic mouse according to claim 5, wherein said muscle specific regulatory element is selected from the group consisting of a myosin light chain promoter, a skeletal alpha actin promoter, a creatine kinase promoter, and an aldolase A promoter.

7. A transgenic mouse having a transgene integrated within its genome, said transgene having a nucleotide sequence which hybridizes under highly stringent hybridization conditions with a nucleic acid having a nucleotide sequence complementary to the nucleotide sequence of SEQ ID NO: 1 or a portion thereof, said sequence encoding an AMP activated protein kinase γ3 subunit or an R225 variant thereof, wherein said transgene is operably linked to a promoter that drives expression in skeletal muscle, and wherein said transgenic mouse has an elevated glycogen content in skeletal muscle.

8. A method for making a transgenic mouse having integrated within its genome, a nucleic acid encoding an AMP activated protein kinase γ3 subunit or an R225 variant thereof, wherein said nucleic acid is linked to a regulatory element that drives expression in skeletal muscle, said method comprising introducing an expression construct into an ovum or an embryo of a mouse, said expression construct comprising said regulatory element operably linked to a nucleotide sequence encoding a polypeptide having at least 85% sequence identity to the amino acid sequence shown in SEQ ID NO:2 or to a portion thereof, and wherein said transgenic mouse has an elevated glycogen content in skeletal muscle.

9. The method according to claim 8, where the expression construct is microinjected into said ovum or embryo of the mouse.

10. A method of identifying a compound or composition effective for altering energy metabolism, said method comprising: (a) administering a test compound or test composition to said transgenic mouse of claim 1; and (b) evaluating the effect of said test compound or test composition on the energy metabolism on said transgenic mouse; wherein said test compound or test composition is identified if energy metabolism is altered.

11. A method for making a transgenic mouse having integrated within its genome, a nucleic acid encoding an AMP activated protein kinase γ3 subunit or an R225 variant thereof, wherein said nucleic acid is linked to a regulatory element that drives expression in skeletal muscle, said method comprising introducing an expression construct into an ovum or an embryo, of a mouse, said expression construct comprising said regulatory element operably linked to a nucleotide sequence having at least 85% sequence identity to the nucleotide sequence shown in SEQ ID NO: 1, and wherein said transgenic mouse has an elevated glycogen content in skeletal muscle.

12. The method according to claim 11, where the expression construct is microinjected into said ovum or embryo of the mouse.

13. A method for making a transgenic mouse having integrated within its genome, a nucleic acid encoding an AMP activated protein kinase γ3 subunit or an R225 variant thereof, said method comprising introducing an expression construct into embryonic stem cells of a mouse, said expression construct comprising a regulatory element operably linked to a nucleotide sequence having at least 85% sequence identity to a nucleotide sequence encoding a polypeptide having at least 85% sequence identity to the amino acid sequence shown in SEQ ID NO: 2 or to a portion thereof; where said regulatory element is capable of mediating expression in skeletal muscle, and wherein said transgenic mouse has an elevated glycogen content in skeletal muscle.

14. The method according to claim 13, where the expression construct is electroporated into said embryonic stem cells.

* * * * *

SEQUENCE LISTING

<160> NUMBER OF SEQ ID NOS: 12

<210> SEQ ID NO 1
<211> LENGTH: 1470
<212> TYPE: DNA
<213> ORGANISM: Homo sapiens
<220> FEATURE:
<221> NAME/KEY: CDS
<222> LOCATION: (1)..(1470)
<223> OTHER INFORMATION:

<400> SEQUENCE: 1

```
atg gag ccc ggg ctg gag cac gca ctg cgc agg acc cct tcc tgg agc      48
Met Glu Pro Gly Leu Glu His Ala Leu Arg Arg Thr Pro Ser Trp Ser
1               5                   10                  15 agc ctt ggg ggt tct gag cat caa gag atg agc ttc cta gag caa gaa      96
Ser Leu Gly Gly Ser Glu His Gln Glu Met Ser Phe Leu Glu Gln Glu
            20                  25                  30 aac agc agc tca tgg cca tca cca gct gtg acc agc agc tca gaa aga     144
Asn Ser Ser Ser Trp Pro Ser Pro Ala Val Thr Ser Ser Ser Glu Arg
        35                  40                  45 atc cgt ggg aaa cgg agg gcc aaa gcc ttg aga tgg aca agg cag aag     192
Ile Arg Gly Lys Arg Arg Ala Lys Ala Leu Arg Trp Thr Arg Gln Lys
    50                  55                  60 tcg gtg gag gaa ggg gag cca cca ggt cag ggg gaa ggt ccc cgg tcc     240
Ser Val Glu Glu Gly Glu Pro Pro Gly Gln Gly Glu Gly Pro Arg Ser
65                  70                  75                  80 agg cca act gct gag tcc acc ggg ctg gag gcc aca ttc ccc aag acc     288
Arg Pro Thr Ala Glu Ser Thr Gly Leu Glu Ala Thr Phe Pro Lys Thr
                85                  90                  95 aca ccc ttg gct caa gct gat cct gcc ggg gtg ggc act cca cca aca     336
Thr Pro Leu Ala Gln Ala Asp Pro Ala Gly Val Gly Thr Pro Pro Thr
            100                 105                 110 ggg tgg gac tgc ctc ccc tct gac tgt aca gcc tca gct gca ggc tcc     384
Gly Trp Asp Cys Leu Pro Ser Asp Cys Thr Ala Ser Ala Ala Gly Ser
        115                 120                 125 agc aca gat gat gtg gag ctg gcc acg gag ttc cca gcc aca gag gcc     432
Ser Thr Asp Asp Val Glu Leu Ala Thr Glu Phe Pro Ala Thr Glu Ala
    130                 135                 140 tgg gag tgt gag cta gaa ggc ctg ctg gaa gag agg cct gcc ctg tgc     480
Trp Glu Cys Glu Leu Glu Gly Leu Leu Glu Glu Arg Pro Ala Leu Cys
145                 150                 155                 160 ctg tcc ccg cag gcc cca ttt ccc aag ctg ggc tgg gat gac gaa ctg     528
Leu Ser Pro Gln Ala Pro Phe Pro Lys Leu Gly Trp Asp Asp Glu Leu
                165                 170                 175 cgg aaa ccc ggc gcc cag atc tac atg cgc ttc atg cag gag cac acc     576
Arg Lys Pro Gly Ala Gln Ile Tyr Met Arg Phe Met Gln Glu His Thr
            180                 185                 190 tgc tac gat gcc atg gca act agc tcc aag cta gtc atc ttc gac acc     624
Cys Tyr Asp Ala Met Ala Thr Ser Ser Lys Leu Val Ile Phe Asp Thr
        195                 200                 205 atg ctg gag atc aag aag gcc ttc ttt gct ctg gtg gcc aac ggt gtg     672
Met Leu Glu Ile Lys Lys Ala Phe Phe Ala Leu Val Ala Asn Gly Val
    210                 215                 220 cgg gca gcc cct cta tgg gac agc aag aag cag agc ttt gtg ggg atg     720
Arg Ala Ala Pro Leu Trp Asp Ser Lys Lys Gln Ser Phe Val Gly Met
225                 230                 235                 240 ctg acc atc act gac ttc atc ctg gtg ctg cat cgc tac tac agg tcc     768
Leu Thr Ile Thr Asp Phe Ile Leu Val Leu His Arg Tyr Tyr Arg Ser
                245                 250                 255
```

```
ccc ctg gtc cag atc tat gag att gaa caa cat aag att gag acc tgg      816
Pro Leu Val Gln Ile Tyr Glu Ile Glu Gln His Lys Ile Glu Thr Trp
        260                 265                 270 agg gag atc tac ctg caa ggc tgc ttc aag cct ctg gtc tcc atc tct      864
Arg Glu Ile Tyr Leu Gln Gly Cys Phe Lys Pro Leu Val Ser Ile Ser
        275                 280                 285 cct aat gat agc ctg ttt gaa gct gtc tac acc ctc atc aag aac cgg      912
Pro Asn Asp Ser Leu Phe Glu Ala Val Tyr Thr Leu Ile Lys Asn Arg
    290                 295                 300 atc cat cgc ctg cct gtt ctt gac ccg gtg tca ggc aac gta ctc cac      960
Ile His Arg Leu Pro Val Leu Asp Pro Val Ser Gly Asn Val Leu His
305                 310                 315                 320 atc ctc aca cac aaa cgc ctg ctc aag ttc ctg cac atc ttt ggt tcc     1008
Ile Leu Thr His Lys Arg Leu Leu Lys Phe Leu His Ile Phe Gly Ser
                325                 330                 335 ctg ctg ccc cgg ccc tcc ttc ctc tac cgc act atc caa gat ttg ggc     1056
Leu Leu Pro Arg Pro Ser Phe Leu Tyr Arg Thr Ile Gln Asp Leu Gly
            340                 345                 350 atc ggc aca ttc cga gac ttg gct gtg gtg ctg gag aca gca ccc atc     1104
Ile Gly Thr Phe Arg Asp Leu Ala Val Val Leu Glu Thr Ala Pro Ile
        355                 360                 365 ctg act gca ctg gac atc ttt gtg gac cgg cgt gtg tct gca ctg cct     1152
Leu Thr Ala Leu Asp Ile Phe Val Asp Arg Arg Val Ser Ala Leu Pro
    370                 375                 380 gtg gtc aac gaa tgt ggt cag gtc gtg ggc ctc tat tcc cgc ttt gat     1200
Val Val Asn Glu Cys Gly Gln Val Val Gly Leu Tyr Ser Arg Phe Asp
385                 390                 395                 400 gtg att cac ctg gct gcc cag caa acc tac aac cac ctg gac atg agt     1248
Val Ile His Leu Ala Ala Gln Gln Thr Tyr Asn His Leu Asp Met Ser
                405                 410                 415 gtg gga gaa gcc ctg agg cag agg aca cta tgt ctg gag gga gtc ctt     1296
Val Gly Glu Ala Leu Arg Gln Arg Thr Leu Cys Leu Glu Gly Val Leu
            420                 425                 430 tcc tgc cag ccc cac gag agc ttg ggg gaa gtg atc gac agg att gct     1344
Ser Cys Gln Pro His Glu Ser Leu Gly Glu Val Ile Asp Arg Ile Ala
        435                 440                 445 cgg gag cag gta cac agg ctg gtg cta gtg gac gag acc cag cat ctc     1392
Arg Glu Gln Val His Arg Leu Val Leu Val Asp Glu Thr Gln His Leu
    450                 455                 460 ttg ggc gtg gtc tcc ctc tcc gac atc ctt cag gca ctg gtg ctc agc     1440
Leu Gly Val Val Ser Leu Ser Asp Ile Leu Gln Ala Leu Val Leu Ser
465                 470                 475                 480 cct gct ggc atc gat gcc ctc ggg gcc tga                             1470
Pro Ala Gly Ile Asp Ala Leu Gly Ala
                485

<210> SEQ ID NO 2
<211> LENGTH: 489
<212> TYPE: PRT
<213> ORGANISM: Homo sapiens

<400> SEQUENCE: 2

Met Glu Pro Gly Leu Glu His Ala Leu Arg Arg Thr Pro Ser Trp Ser
1               5                   10                  15

Ser Leu Gly Gly Ser Glu His Gln Glu Met Ser Phe Leu Glu Gln Glu
            20                  25                  30

Asn Ser Ser Ser Trp Pro Ser Pro Ala Val Thr Ser Ser Ser Glu Arg
        35                  40                  45

Ile Arg Gly Lys Arg Arg Ala Lys Ala Leu Arg Trp Thr Arg Gln Lys
```

```
                50                  55                  60
Ser Val Glu Glu Gly Glu Pro Gly Gln Gly Glu Gly Pro Arg Ser
 65                  70                  75                  80

Arg Pro Thr Ala Glu Ser Thr Gly Leu Glu Ala Thr Phe Pro Lys Thr
                 85                  90                  95

Thr Pro Leu Ala Gln Ala Asp Pro Ala Gly Val Gly Thr Pro Pro Thr
                100                 105                 110

Gly Trp Asp Cys Leu Pro Ser Asp Cys Thr Ala Ser Ala Ala Gly Ser
                115                 120                 125

Ser Thr Asp Asp Val Glu Leu Ala Thr Glu Phe Pro Ala Thr Glu Ala
130                 135                 140

Trp Glu Cys Glu Leu Glu Gly Leu Leu Glu Glu Arg Pro Ala Leu Cys
145                 150                 155                 160

Leu Ser Pro Gln Ala Pro Phe Pro Lys Leu Gly Trp Asp Asp Glu Leu
                165                 170                 175

Arg Lys Pro Gly Ala Gln Ile Tyr Met Arg Phe Met Gln Glu His Thr
                180                 185                 190

Cys Tyr Asp Ala Met Ala Thr Ser Ser Lys Leu Val Ile Phe Asp Thr
                195                 200                 205

Met Leu Glu Ile Lys Lys Ala Phe Phe Ala Leu Val Ala Asn Gly Val
210                 215                 220

Arg Ala Ala Pro Leu Trp Asp Ser Lys Lys Gln Ser Phe Val Gly Met
225                 230                 235                 240

Leu Thr Ile Thr Asp Phe Ile Leu Val Leu His Arg Tyr Tyr Arg Ser
                245                 250                 255

Pro Leu Val Gln Ile Tyr Glu Ile Glu Gln His Lys Ile Glu Thr Trp
                260                 265                 270

Arg Glu Ile Tyr Leu Gln Gly Cys Phe Lys Pro Leu Val Ser Ile Ser
                275                 280                 285

Pro Asn Asp Ser Leu Phe Glu Ala Val Tyr Thr Leu Ile Lys Asn Arg
                290                 295                 300

Ile His Arg Leu Pro Val Leu Asp Pro Val Ser Gly Asn Val Leu His
305                 310                 315                 320

Ile Leu Thr His Lys Arg Leu Leu Lys Phe Leu His Ile Phe Gly Ser
                325                 330                 335

Leu Leu Pro Arg Pro Ser Phe Leu Tyr Arg Thr Ile Gln Asp Leu Gly
                340                 345                 350

Ile Gly Thr Phe Arg Asp Leu Ala Val Val Leu Glu Thr Ala Pro Ile
                355                 360                 365

Leu Thr Ala Leu Asp Ile Phe Val Asp Arg Arg Val Ser Ala Leu Pro
370                 375                 380

Val Val Asn Glu Cys Gly Gln Val Val Gly Leu Tyr Ser Arg Phe Asp
385                 390                 395                 400

Val Ile His Leu Ala Ala Gln Thr Tyr Asn His Leu Asp Met Ser
                405                 410                 415

Val Gly Glu Ala Leu Arg Gln Arg Thr Leu Cys Leu Glu Gly Val Leu
                420                 425                 430

Ser Cys Gln Pro His Glu Ser Leu Gly Glu Val Ile Asp Arg Ile Ala
                435                 440                 445

Arg Glu Gln Val His Arg Leu Val Leu Val Asp Glu Thr Gln His Leu
                450                 455                 460

Leu Gly Val Val Ser Leu Ser Asp Ile Leu Gln Ala Leu Val Leu Ser
465                 470                 475                 480
```

```
Pro Ala Gly Ile Asp Ala Leu Gly Ala
            485

<210> SEQ ID NO 3
<211> LENGTH: 1518
<212> TYPE: DNA
<213> ORGANISM: Mus musculus
<220> FEATURE:
<221> NAME/KEY: CDS
<222> LOCATION: (13)..(1482)
<223> OTHER INFORMATION:

<400> SEQUENCE: 3
agagctggcc gc atg gag ccc gag ctg gag cac aca ttg cct ggg acc ctg      51
              Met Glu Pro Glu Leu Glu His Thr Leu Pro Gly Thr Leu
                1               5                  10 acc tgg agc cac agt ggg ggt cca gag agt caa gag atg gac ttc tta        99
Thr Trp Ser His Ser Gly Gly Pro Glu Ser Gln Glu Met Asp Phe Leu
 15                  20                  25 gaa caa gga gaa aac tca tgg ccc tca cca gct gtg gcc acc agc tca       147
Glu Gln Gly Glu Asn Ser Trp Pro Ser Pro Ala Val Ala Thr Ser Ser
 30                  35                  40                  45 gaa aga acc tgt gcc ata cgg gga gtc aag gct tcc aga tgg acg aga       195
Glu Arg Thr Cys Ala Ile Arg Gly Val Lys Ala Ser Arg Trp Thr Arg
                 50                  55                  60 cag gag gcc gta gag gaa gca gaa cca cca ggt ttg gga gaa ggt gcc       243
Gln Glu Ala Val Glu Glu Ala Glu Pro Pro Gly Leu Gly Glu Gly Ala
             65                  70                  75 cag tcc aga cca gct gct gag tcc acc agg cag gag gcc aca ttc ccg       291
Gln Ser Arg Pro Ala Ala Glu Ser Thr Arg Gln Glu Ala Thr Phe Pro
         80                  85                  90 aag gcc aca ccc ttg gct caa gct gtt ccc ttg gct gaa gcg gag acc       339
Lys Ala Thr Pro Leu Ala Gln Ala Val Pro Leu Ala Glu Ala Glu Thr
     95                 100                 105 tcc ccc aca ggg tgg gac ctg ctc ttg ccc gac tgt gca gcc tca gca       387
Ser Pro Thr Gly Trp Asp Leu Leu Leu Pro Asp Cys Ala Ala Ser Ala
110                 115                 120                 125 ggg ggc tcc agc aca ggt gac ctg gag ctg acc ata gag ttc cca gcc       435
Gly Gly Ser Ser Thr Gly Asp Leu Glu Leu Thr Ile Glu Phe Pro Ala
                130                 135                 140 cca gag gcc tgg gac tgt gag ctg gaa ggc ctg ggg aag gac agg cct       483
Pro Glu Ala Trp Asp Cys Glu Leu Glu Gly Leu Gly Lys Asp Arg Pro
            145                 150                 155 cgt cct ggt cca tcc cca cag gcc cca ctt ctc ggc ctg agt tgg gat       531
Arg Pro Gly Pro Ser Pro Gln Ala Pro Leu Leu Gly Leu Ser Trp Asp
        160                 165                 170 gac gaa ctt cag aag ccc gga gcc cag gtc tac atg cac ttc atg cag       579
Asp Glu Leu Gln Lys Pro Gly Ala Gln Val Tyr Met His Phe Met Gln
    175                 180                 185 gaa cac acc tgt tat gat gcc atg gct acc agc tcc aaa ttg gtc atc       627
Glu His Thr Cys Tyr Asp Ala Met Ala Thr Ser Ser Lys Leu Val Ile
190                 195                 200                 205 ttt gac acc acg ttg gag ata aag aag gct ttc ttt gcc atg gtg gcc       675
Phe Asp Thr Thr Leu Glu Ile Lys Lys Ala Phe Phe Ala Met Val Ala
                210                 215                 220 aac ggt gtg agg gca gct cct ctg tgg gac agc aag aag cag agc ttt       723
Asn Gly Val Arg Ala Ala Pro Leu Trp Asp Ser Lys Lys Gln Ser Phe
            225                 230                 235 gtg ggt atg ctc acc atc act gac ttt atc ctg gtg ctg cac cgg tac       771
Val Gly Met Leu Thr Ile Thr Asp Phe Ile Leu Val Leu His Arg Tyr
        240                 245                 250
```

```
tac aga tcc ccc ctg gtc cag atc tat gag att gaa gaa cat aag att      819
Tyr Arg Ser Pro Leu Val Gln Ile Tyr Glu Ile Glu Glu His Lys Ile
    255                 260                 265 gag acc tgg agg gag atc tac cta caa ggc tgc ttc aag cct cta gtc      867
Glu Thr Trp Arg Glu Ile Tyr Leu Gln Gly Cys Phe Lys Pro Leu Val
270                 275                 280                 285 tcc atc tct ccc aat gac agc ctg ttt gaa gct gtc tat gcc ctc atc      915
Ser Ile Ser Pro Asn Asp Ser Leu Phe Glu Ala Val Tyr Ala Leu Ile
                290                 295                 300 aag aac cga atc ccc cgc ctg ccg gtc ctg gac ccg gtc tct ggc act      963
Lys Asn Arg Ile Pro Arg Leu Pro Val Leu Asp Pro Val Ser Gly Thr
            305                 310                 315 gtg ctc tac ata ctc aca cac aag cgg cta ctc aag ttc ctg cat ata     1011
Val Leu Tyr Ile Leu Thr His Lys Arg Leu Leu Lys Phe Leu His Ile
        320                 325                 330 ttt ggt gcc ctg ttg ccc cgg ccc tcc ttc ctc tgc cgc act atc caa     1059
Phe Gly Ala Leu Leu Pro Arg Pro Ser Phe Leu Cys Arg Thr Ile Gln
    335                 340                 345 gac ttg ggc atc ggc aca ttc cga gat ttg gct gta gtt ctg gaa aca     1107
Asp Leu Gly Ile Gly Thr Phe Arg Asp Leu Ala Val Val Leu Glu Thr
350                 355                 360                 365 gct cct gtc ctg act gcg ctg gac atc ttt gtg gac cga cgt gtg tct     1155
Ala Pro Val Leu Thr Ala Leu Asp Ile Phe Val Asp Arg Arg Val Ser
                370                 375                 380 gca ctg cct gtg gtc aat gaa tct ggt cag gtc gtg ggc ctc tac tcc     1203
Ala Leu Pro Val Val Asn Glu Ser Gly Gln Val Val Gly Leu Tyr Ser
            385                 390                 395 cgc ttt gat gtc att cac ctg gct gcc cag caa acc tac aac cac cta     1251
Arg Phe Asp Val Ile His Leu Ala Ala Gln Gln Thr Tyr Asn His Leu
        400                 405                 410 gac atg agt gtg gga gaa gct ctg aga cag agg aca ctg tgt ctg gag     1299
Asp Met Ser Val Gly Glu Ala Leu Arg Gln Arg Thr Leu Cys Leu Glu
    415                 420                 425 gga gtt ctc tcc tgc cag ccc cac gag agc cta ggt gaa gtc att gac     1347
Gly Val Leu Ser Cys Gln Pro His Glu Ser Leu Gly Glu Val Ile Asp
430                 435                 440                 445 agg atc gca cgg gaa cag gtg cat agg ctg gtg ttg gtg gat gag acc     1395
Arg Ile Ala Arg Glu Gln Val His Arg Leu Val Leu Val Asp Glu Thr
                450                 455                 460 cag cat ctt ctg ggc gtg gtc tcc ctc tct gac ata ctt caa gca ctg     1443
Gln His Leu Leu Gly Val Val Ser Leu Ser Asp Ile Leu Gln Ala Leu
            465                 470                 475 gta ctc agc cct gct ggc atc gat gcc ctc agc gcc tga gacctgagtc      1492
Val Leu Ser Pro Ala Gly Ile Asp Ala Leu Ser Ala
        480                 485 ctcacaccca agccatcttc ttcacc                                        1518

<210> SEQ ID NO 4
<211> LENGTH: 489
<212> TYPE: PRT
<213> ORGANISM: Mus musculus

<400> SEQUENCE: 4

Met Glu Pro Glu Leu Glu His Thr Leu Pro Gly Thr Leu Thr Trp Ser
1               5                   10                  15

His Ser Gly Gly Pro Glu Ser Gln Glu Met Asp Phe Leu Glu Gln Gly
                20                  25                  30

Glu Asn Ser Trp Pro Ser Pro Ala Val Ala Thr Ser Ser Glu Arg Thr
            35                  40                  45
```

-continued

```
Cys Ala Ile Arg Gly Val Lys Ala Ser Arg Trp Thr Arg Gln Glu Ala
     50                  55                  60
Val Glu Glu Ala Glu Pro Pro Gly Leu Gly Glu Gly Ala Gln Ser Arg
 65                  70                  75                  80
Pro Ala Ala Glu Ser Thr Arg Gln Glu Ala Thr Phe Pro Lys Ala Thr
                 85                  90                  95
Pro Leu Ala Gln Ala Val Pro Leu Ala Glu Ala Glu Thr Ser Pro Thr
                100                 105                 110
Gly Trp Asp Leu Leu Pro Asp Cys Ala Ala Ser Ala Gly Gly Ser
         115                 120                 125
Ser Thr Gly Asp Leu Glu Leu Thr Ile Glu Phe Pro Ala Pro Glu Ala
    130                 135                 140
Trp Asp Cys Glu Leu Glu Gly Leu Gly Lys Asp Arg Pro Arg Pro Gly
145                 150                 155                 160
Pro Ser Pro Gln Ala Pro Leu Leu Gly Leu Ser Trp Asp Asp Glu Leu
                165                 170                 175
Gln Lys Pro Gly Ala Gln Val Tyr Met His Phe Met Gln Glu His Thr
            180                 185                 190
Cys Tyr Asp Ala Met Ala Thr Ser Ser Lys Leu Val Ile Phe Asp Thr
        195                 200                 205
Thr Leu Glu Ile Lys Lys Ala Phe Phe Ala Met Val Ala Asn Gly Val
    210                 215                 220
Arg Ala Ala Pro Leu Trp Asp Ser Lys Lys Gln Ser Phe Val Gly Met
225                 230                 235                 240
Leu Thr Ile Thr Asp Phe Ile Leu Val Leu His Arg Tyr Tyr Arg Ser
                245                 250                 255
Pro Leu Val Gln Ile Tyr Glu Ile Glu His Lys Ile Glu Thr Trp
            260                 265                 270
Arg Glu Ile Tyr Leu Gln Gly Cys Phe Lys Pro Leu Val Ser Ile Ser
        275                 280                 285
Pro Asn Asp Ser Leu Phe Glu Ala Val Tyr Ala Leu Ile Lys Asn Arg
    290                 295                 300
Ile Pro Arg Leu Pro Val Leu Asp Pro Val Ser Gly Thr Val Leu Tyr
305                 310                 315                 320
Ile Leu Thr His Lys Arg Leu Leu Lys Phe Leu His Ile Phe Gly Ala
                325                 330                 335
Leu Leu Pro Arg Pro Ser Phe Leu Cys Arg Thr Ile Gln Asp Leu Gly
            340                 345                 350
Ile Gly Thr Phe Arg Asp Leu Ala Val Val Leu Glu Thr Ala Pro Val
        355                 360                 365
Leu Thr Ala Leu Asp Ile Phe Val Asp Arg Arg Val Ser Ala Leu Pro
    370                 375                 380
Val Val Asn Glu Ser Gly Gln Val Val Gly Leu Tyr Ser Arg Phe Asp
385                 390                 395                 400
Val Ile His Leu Ala Ala Gln Gln Thr Tyr Asn His Leu Asp Met Ser
                405                 410                 415
Val Gly Glu Ala Leu Arg Gln Arg Thr Leu Cys Leu Glu Gly Val Leu
            420                 425                 430
Ser Cys Gln Pro His Glu Ser Leu Gly Glu Val Ile Asp Arg Ile Ala
        435                 440                 445
Arg Glu Gln Val His Arg Leu Val Leu Val Asp Glu Thr Gln His Leu
    450                 455                 460
```

-continued

```
Leu Gly Val Val Ser Leu Ser Asp Ile Leu Gln Ala Leu Val Leu Ser
465                 470                 475                 480

Pro Ala Gly Ile Asp Ala Leu Ser Ala
                485
```

<210> SEQ ID NO 5
<211> LENGTH: 9100
<212> TYPE: DNA
<213> ORGANISM: Homo sapiens
<220> FEATURE:
<221> NAME/KEY: CDS
<222> LOCATION: (991)..(1023)
<223> OTHER INFORMATION:
<220> FEATURE:
<221> NAME/KEY: CDS
<222> LOCATION: (1386)..(1425)
<223> OTHER INFORMATION:
<220> FEATURE:
<221> NAME/KEY: CDS
<222> LOCATION: (1860)..(2015)
<223> OTHER INFORMATION:
<220> FEATURE:
<221> NAME/KEY: CDS
<222> LOCATION: (2380)..(2784)
<223> OTHER INFORMATION:
<220> FEATURE:
<221> NAME/KEY: CDS
<222> LOCATION: (4162)..(4243)
<223> OTHER INFORMATION:
<220> FEATURE:
<221> NAME/KEY: CDS
<222> LOCATION: (4701)..(4759)
<223> OTHER INFORMATION:
<220> FEATURE:
<221> NAME/KEY: CDS
<222> LOCATION: (4885)..(4930)
<223> OTHER INFORMATION:
<220> FEATURE:
<221> NAME/KEY: CDS
<222> LOCATION: (5134)..(5188)
<223> OTHER INFORMATION:
<220> FEATURE:
<221> NAME/KEY: CDS
<222> LOCATION: (5390)..(5516)
<223> OTHER INFORMATION:
<220> FEATURE:
<221> NAME/KEY: CDS
<222> LOCATION: (5670)..(5835)
<223> OTHER INFORMATION:
<220> FEATURE:
<221> NAME/KEY: CDS
<222> LOCATION: (8187)..(8224)
<223> OTHER INFORMATION:
<220> FEATURE:
<221> NAME/KEY: CDS
<222> LOCATION: (8395)..(8541)
<223> OTHER INFORMATION:
<220> FEATURE:
<221> NAME/KEY: CDS
<222> LOCATION: (8885)..(8997)
<223> OTHER INFORMATION:

<400> SEQUENCE: 5

```
taataaactc agacagaaat tcaccagtct gttgttgagt gtccactcca gggccagggc      60
tgggatggaa gaggctggaa ggaggagaga aagggagggg cagagagagg aaagccggag     120
cagctgggtc agcattccca atccggacat tgactcaggc tccgggaatg ccaaggaaga     180
gggtggcagc tactggagcc aggctgggat cctgttggca ccaggatgt aggcacagca      240 ctcacagagg gttgggggct gggacacctg cacacccagg catatctccc aaccacaggt     300
ggaaacagat gtctcttccc ctgcggggag ctctgagtgc tccccacgcc ttcgaggtga     360
ttctcacagc tcttcacctg cctgaaacac ccactccatc tccttcacct gagagaggga     420
```

```
cacactccag ggactcaaat ctggacatct ggacatacac tagctgctct cctggactac      480
ccacaaaccc cttgcctcat ctccagcctc tgagctggct gcaacttgcc ctttctaact      540
ccagcaccac cctctactga aattagaaca aggaagaaag ttatgctgat ctgcctccat      600
gttcccttct ttggtgcctg ataaagatga gggaggctct tggaataggg gctcaggact      660
ctgagagccc aactctgctc aatgaccatg ttcccacatg ctccaagcca catccctca       720 aaaagggtcc ctctagcttg tcctcagtga cccaggaggc agctgaggac caagtaccca      780
gattatccgg tgcgcccctt ccctcccagc aaccccagc cttcagggct gtagcagctg       840
agcaaatggg ggccctccc tctcattgcc tgacacccaa tcagagagaa accgatcctg       900
gcagggcagg gtgcccgggg ccgggcccag aatagtgcag cccagccaca gtgtcgcaca      960
cttgctctca gttggtctgg ggctggccac atg gag ccc ggg ctg gag cac gca     1014
                                 Met Glu Pro Gly Leu Glu His Ala
                                  1               5 ctg cgc agg gtatgggggt cccaggggag ccggagccgg ggcagctgag                1063
Leu Arg Arg
        10 gccagaagat tgagcgcacg ggctgtgaat gtgtgtgtgg gcgtgtgtgt cttctggtgt      1123 gtgtttggtc tggatttct cgtgaatatg gcatgtgca tgtttgggca tatgtattgt       1183 gagtgtgtgt ggttctgtgt gcctgggagt gttttggatgt gtgtgtttct gtgtgtgttt   1243 gtgtatggct gcatgtctgt gtatggcgtg tgtctgagcg tgtgtattgg gtgcatggg     1303 tgtgtaggcg tgtgttcagg gagaagggt ttgggaatgt aaggcacttt ccccactcct      1363 tcagaaactc ttctccccac ag acc cct tcc tgg agc agc ctt ggg ggt tct     1415
                        Thr Pro Ser Trp Ser Ser Leu Gly Gly Ser
                                     15                  20 gag cat caa g gtaggagaa tgcccctcc ctggggccta acctcttccc              1465
Glu His Gln ccacctcctt gtcccccact tttctgggac cccaattccc tcccagcctg cttttatct      1525 tcctcctttt ggtctttctt cctcattgtt cttcctcctt tccccaggtg tgtttccctc     1585
acctccaatt tcctcttttc agaagtgact ttcccactta cttgctgtgt gatttgcagc    1645
aaattgctta acctctctga atttctggtc cctcactagc aaaatagga tgataataat     1705 gcctgctta taaggctgct gtaagttta aatgagaaat atgttggaga aaagcccatt      1765
ggaagcttgc aaatcctaaa gattatgaat aacatttgaa ttgattttga tgcattactc    1825
cctattaacc aaacaggccc cattcccctt ccag ag  atg agc ttc cta gag caa    1879
                                        Glu Met Ser Phe Leu Glu Gln
                                                              30 gaa aac agc agc tca tgg cca tca cca gct gtg acc agc agc tca gaa       1927
Glu Asn Ser Ser Ser Trp Pro Ser Pro Ala Val Thr Ser Ser Ser Glu
        35                  40                  45 aga atc cgt ggg aaa cgg agg gcc aaa gcc ttg aga tgg aca agg cag       1975
Arg Ile Arg Gly Lys Arg Arg Ala Lys Ala Leu Arg Trp Thr Arg Gln
    50                  55                  60 aag tcg gtg gag gaa ggg gag cca cca ggt cag ggg gaa g gtgaggccaa      2025
Lys Ser Val Glu Glu Gly Glu Pro Pro Gly Gln Gly Glu
65                  70                  75 ggccagttct ggggaggtgg gagccagggg agtgggaaat cccagaggag cctggtctg      2085 gtctctacct caggtccctc cataacacag agttggaccc aaccttcatc ttgtggcctc     2145
agtctcccta catagtagag aacaaggcac tgcagtgcca gaggccagca tggccaactc     2205
agaaagatgg gacagagcca ctacctgggg cgactctcag gtcagcccct cacctgcaaa     2265
```

```
tagggccaca gcatccaggc ttcccactgc tgctgtgaga tgaatggcga cagcagatga    2325
gaacgtgctt tggaagatgg agttactgtc ctcttcccct cctcccccaa acag gt       2381
                                                              Gly ccc cgg tcc agg cca gct gct gag tcc acc ggg ctg gag gcc aca ttc      2429
Pro Arg Ser Arg Pro Ala Ala Glu Ser Thr Gly Leu Glu Ala Thr Phe
         80                  85                  90 ccc aag acc aca ccc ttg gct caa gct gat cct gcc ggg gtg ggc act      2477
Pro Lys Thr Thr Pro Leu Ala Gln Ala Asp Pro Ala Gly Val Gly Thr
     95                 100                 105 cca cca aca ggg tgg gac tgc ctc ccc tct gac tgt aca gcc tca gct      2525
Pro Pro Thr Gly Trp Asp Cys Leu Pro Ser Asp Cys Thr Ala Ser Ala
110                 115                 120                 125 gca ggc tcc agc aca gat gat gtg gag ctg gcc acg gag ttc cca gcc      2573
Ala Gly Ser Ser Thr Asp Asp Val Glu Leu Ala Thr Glu Phe Pro Ala
                130                 135                 140 aca gag gcc tgg gag tgt gag cta gaa ggc ctg ctg gaa gag agg cct      2621
Thr Glu Ala Trp Glu Cys Glu Leu Glu Gly Leu Leu Glu Glu Arg Pro
            145                 150                 155 gcc ctg tgc ctg tcc ccg cag gcc cca ttt ccc aag ctg ggc tgg gat      2669
Ala Leu Cys Leu Ser Pro Gln Ala Pro Phe Pro Lys Leu Gly Trp Asp
        160                 165                 170 gac gaa ctg cgg aaa ccc ggc gcc cag atc tac atg cgc ttc atg cag      2717
Asp Glu Leu Arg Lys Pro Gly Ala Gln Ile Tyr Met Arg Phe Met Gln
    175                 180                 185 gag cac acc tgc tac gat gcc atg gca act agc tcc aag cta gtc atc      2765
Glu His Thr Cys Tyr Asp Ala Met Ala Thr Ser Ser Lys Leu Val Ile
190                 195                 200                 205 ttc gac acc atg ctg gag g tgaggccacg gctctgccca acctgtactc           2814
Phe Asp Thr Met Leu Glu
                210 actctccatc cacacggtgc tgcagccgcc actcccaccc tgcaggatgc cctgctgagc    2874 caggtgcccc tgcaagcccc ctgaaaggac tccttcttag cactatggag gccagttggg    2934 ggagggacag cttctactct ctgttagcac acgtaattgt catcacagct ctgccactta    2994 gtagctgtag gaccttgagt tacattacct ttcttgtctc taaaatgggg atcgaaatgc    3054 ctgctgcacc ctacatagtt cagaggattc ttggactacc cagtataaag cgtgaacaaa    3114 gtatgtgtaa gacattgcag aggccgggca cggtggctca tgtctgtaat cccagcactt    3174 taggaggtcg aggtgggcaa atcacaaggt caggagttcg agaccggcct gaccaacatg    3234 gtgaaacccc atctctacta aaaaaaaaa tacaaaaaat tagccggccg tggtggtggg     3294 cgcctgtaat cccagctact ttggaggctg aggtaggcga atcacttgaa cccaggaggc    3354 agaggttgca gtgagccgag atcgtgccac tgcactccag cccgggagac agtgcgaaat    3414 tccatgtcaa aaaaaaaaaa aggcatcaca gagtgactta gaaaaagag taggggactc     3474 tcttggtaac agaaaaaata atgagctctg gcacctgctc ttccattagg cttagctata    3534 aatgtctata atcttattct tatcattgtt atgcagtgca gtgtttccca aaacacggtg    3594 tatgtattgt ccatagcatg cattttgatt ctaatggttc gtgaaaaaat atgtctattt    3654 cagtagcttt atatttgttt taggctgtgt taaaaaaata taaccagcat gtgcagatag    3714 tactgcttag gacggggcac aaaatgagtc aatataaaat ttatctacaa aaaagtatg    3774 taaatatgca agtgttatgt aaataactat gcctccggta cttagtctat caaaaactag    3834 actgtgtctg tacacacata ccctccaaat ggaaacatga acttagaatt tctcactccc    3894 tggtgtgcca ggtgagggc tcatggtctc aggccacagc cttatctatg tacatgtccc     3954
```

-continued

```
cagcaacgat catgtctagc gtgtactgtg acatgaggaa acaggccag ctggtgtaga        4014 ggagggtcca ggagaaggcc ccatggaaga accctgggtg ggacaggag gggacagcag        4074 gcagatggga ggtgcgcact gaggggcaga gaggggggtg agggtctctc gggacccacc      4134
cttgactgtt ctccctggcc cctcaga tc  aag aag gcc ttc ttt gct ctg gtg      4187
                                Val Lys Lys Ala Phe Phe Ala Leu Val
                                    215                     220 gcc aac ggt gtg cgg gca gcc cct cta tgg gac agc aag aag cag agc        4235
Ala Asn Gly Val Arg Ala Ala Pro Leu Trp Asp Ser Lys Lys Gln Ser
            225                 230                 235 ttt gtg gg  tgaggagagg ctggggaggt gaagggagat ggaggaggtg                4283
Phe Val Gly agggggagat cttgtacggt tgttctgggg ctgatctctg atataccaca agcttggctt      4343
caggccaagc ccagccaggg gccagggtgg aggaaagtcc atccggagtc tgcatggcca      4403
gctgggagac cctggggctc aatttcccca tctgtggagc cgctatgacc agctgacacc      4463
tttcacctcc gctactgcat ggccctgtgc cataggtgct agggagcaaa tgggggagg       4523 caggagagaa agagccccac ttctcaggcc tgggggctg cccactgtc ctgttcccac        4583 agtccccact gtgtctcagc acaaggacac tggcagggtg gggaggggat ctgaccctca      4643
acctgccttc cacccaaagg ccccgggctg acctcctccc cgcccctccc ctgcagg g       4701 atg ctg acc atc act gac ttc atc ctg gtg ctg cat cgc tac tac agg       4749

Met Leu Thr Ile Thr Asp Phe Ile Leu Val Leu His Arg Tyr Tyr Arg
240             245                 250                 255 tcc ccc ctg g tgaggagtgg gctgggaatc ttatgggcac ccagaggggc              4799
Ser Pro Leu gggggcggag gggagtcctc ctggagcctg gtgccctaga agcccacgtc tttctgactt      4859
ctggagtcct gtcgatgtct ctagg tc  cag atc tat gag att gaa caa cat        4910
                                Val Gln Ile Tyr Glu Ile Glu Gln His
                                    260                 265 aag att gag acc tgg agg gg  tgagtgggga gaggaacccg gaaagggctg           4960
Lys Ile Glu Thr Trp Arg Gly
        270 ttggtgatgg tgggccaggg cttaaggtgg aggatgggca gtgggatgt cctggagtga       5020 acaggggagg gacaatagga gcctcgggtg cctgacggaa gggaagctgc ctgggactgc      5080 aaggtgaggc aggtgaccgg ctcccctggc ctgactctgg ctctttctgc aga g atc       5137
                                                                Ile
                                                                275 tac ctg caa ggc tgc ttc aag cct ctg gtc tcc atc tct cct aat gat        5185
Tyr Leu Gln Gly Cys Phe Lys Pro Leu Val Ser Ile Ser Pro Asn Asp
            280                 285                 290 agg tgggtgtctc tgctcattca cctgagcctc ctcctcccac agtccccttc             5238
Arg cccagtccca ctcagctctg aactcacctc ttcatcctag gcggcacaca gacaagggag      5298
ccttggtgcc ctgccctcct tttaggggc ctgggatgga ggttgtctct ccctaggctg       5358
ccccgaggct cactgctccc atctctgcag c ctg ttt gaa gct gtc tac acc         5410
                                  Leu Phe Glu Ala Val Tyr Thr
                                                     295 ctc atc aag aac cgg atc cat cgc ctg cct gtt ctt gac ccg gtg tca        5458
Leu Ile Lys Asn Arg Ile His Arg Leu Pro Val Leu Asp Pro Val Ser
300             305                 310                 315 ggc aac gta ctc cac atc ctc aca cac aaa cgc ctg ctc aag ttc ctg        5506
Gly Asn Val Leu His Ile Leu Thr His Lys Arg Leu Leu Lys Phe Leu
```

|  |  |
|---|---|
| 320       325       330 | |
| cac atc ttt g taagcctggg cccaggtggg aggaaggggg agacctgggc<br>His Ile Phe | 5556 |
| aggtgatcag agggcctgag gagtcttcag ccctagcagt cgtggggaag agctgggagc | 5616 |
| cctcttgaag ctgctggatc cctgatctcc acctggtccc catcctaacc agg gt<br>                                                          Gly | 5671 |
| tcc ctg ctg ccc cgg ccc tcc ttc ctc tac cgc act atc caa gat ttg<br>Ser Leu Leu Pro Arg Pro Ser Phe Leu Tyr Arg Thr Ile Gln Asp Leu<br>            340               345               350 | 5719 |
| ggc atc ggc aca ttc cga gac ttg gct gtg gtg ctg gag aca gca ccc<br>Gly Ile Gly Thr Phe Arg Asp Leu Ala Val Val Leu Glu Thr Ala Pro<br>        355               360               365 | 5767 |
| atc ctg act gca ctg gac atc ttt gtg gac cgg cgt gtg tct gca ctg<br>Ile Leu Thr Ala Leu Asp Ile Phe Val Asp Arg Arg Val Ser Ala Leu<br>        370               375               380 | 5815 |
| cct gtg gtc aac gaa tgt gg  tacccacccc caggatgaga ggctcgggct<br>Pro Val Val Asn Glu Cys Gly<br>    385 | 5865 |
| gggctgggc ctgggagaac ctggtgggga gaatatggga agggcagggt ttctcatgcc | 5925 |
| atccctgtgg ggggtacagg atggactggg gattagaagt ctccgtctac tctgagactt | 5985 |
| gggcaagttg cttagcctct ctgtgcctca gtttcctcct ttgtgaaatg ggattcttca | 6045 |
| caacactcat ctttctgact tcacaggagg atttaaaagg ttatgtgcat gaaaatgggc | 6105 |
| atagcgagag gaagcagcag attttagttt cagttcatct taaaatggag ccggacacgt | 6165 |
| ggtgcatggc tgtaatgcca gccctttgag agaggccaga gcgagaaggt cgcttgaggc | 6225 |
| caggagtttg agtttacata cagtgacact ccaacctggg caacagagca agaccctgtc | 6285 |
| tctaaaataa taatacgaa ataataaaat ttaaaaaatt aaatgtgcca tgggacctcg | 6345 |
| ggcccccagc cagccctcaa tttcctacac tgaaaaaggg ctgcagaaat gacaagatta | 6405 |
| tttctttggt tgaatgatgg ctatgaaata tttcaaagct aaaatcacca taattaagat | 6465 |
| agatatcaag aagtgttttc aatttatttt tgattataaa aaacttcaaa tgtatagaaa | 6525 |
| tggtagaaag aaattgcata atgaaccacc tatatccatt gcctagatta actactgtta | 6585 |
| ctatattgcc ataaccagtt catcttttc tctgaagtaa ttcaaagtaa attacagaca | 6645 |
| tcatgtcatt tcacccctaa acactttagt ctgcacttct aaaacaagt gtattttgg | 6705 |
| ccaggggcgg tggctcatgc ctgtaatccc agcactttgg gaggccaagg tgggcggatc | 6765 |
| acgaggtcaa gagatcgaga ctatcctggc caatatgatg aaaccccatc tctactaaaa | 6825 |
| ctacaaaaaa aaattagctg ggcatggtgg cgcacacctc tagtcccagc tacttaggag | 6885 |
| gctgaggtag gagaatcggt tgaacctggg aggcagaggt tgcagtgagc caagatcgcg | 6945 |
| ccactgtact ccagcctggc aacagagcga gactccaaaa aaaaaaaaaa aaagtgcatt | 7005 |
| ttataccacc aaacaaaacc atgaataatt catattattg tctgacatcc aatccttatt | 7065 |
| ctcacttctc catttcctca agaatgttgg gtattttgt tgttgttttg ggatggagtc | 7125 |
| tccctctgtc actcaggcta aagtgcagtg gtgccatctc ggctcactgc aacctctgcc | 7185 |
| tcccgagttc aagtgattct tgtgcctcag cctcctgagt agctggatt acaggcaaat | 7245 |
| gacaccacgc ccagctaatt ttttgggggt atttttagta gagatgaggt ttcaccatat | 7305 |
| aggccaggcc agtctccaac tcctgacctc aagtgatcca cctgtcttgg cctcccaaag | 7365 |
| tgttgggatt acaggcatga gccaccgcga ccggccaaga atttttttt tttttttttt | 7425 |
| tgagacagag tcttgctctg tcgcctgggc tagaatgcaa tggtgcaatc ttggctcact | 7485 |

```
gcaacctcca cctcccagat tcaagcaatt ctcctgcctc agccgcccaa atagctgggt      7545
ttacaggtgc gtgccatcac acctggctaa ttttttgtat ctttagtaga gatggggttt      7605
cactatgttg gccaggctgg ttttgaactc ctgaccttgt gatccaccca cctcggcctc      7665
ccaagggaat gtattttca tagttgatgt gttcaaaaca ggatccaatt gaagtccatg       7725
gtttacattc gtgtcttttg ttccttaaat ctctttaaat ctataacagc tccattcccc      7785
ctaaattgtt atgacgtggg tgagttgaaa agcctgggtc agttgtccta taggataccc     7845
cacatccaga tttgtctgtt tgctttctag gctggcctt tactttgttc tctattcctg       7905
ggtttcctgt aaactgaaat tatatctaaa gcttgaaga gatttgggca ataaattcga       7965
ggctagacta ttttgtaggt ggtgccatgt tactcacact gcatttcctc aggatgctca     8025
atgtcaggct gtctcactct gggatgctaa gtttgatcct tgggttctgg tagtggcacc    8085
ctgatgcaaa tagccctagg ccctctacac agcaccccgg ttctgaccgg agcctcttcc     8145
ctgtctttct ccccccaccc cccacaacca ccctctgcag g t cag gtc gtg ggc       8199
                                               Gln Val Val Gly ctc tat tcc cgc ttt gat gtg att g taagtgtcgc tggaaaggtg                8244
Leu Tyr Ser Arg Phe Asp Val Ile
395                 400 ggatgctgca gggaggctaa gggtgtgggg atgggtgggg ggcctctgtg gaccagggg      8304 accttgacaa gtatgcaggg gttgacatct gtagggtagg agcccaggca aggggtgac      8364 taggagccat acttctctct ctgccccagc ac ctg gct gcc cag caa acc tac       8417
                                   Asp Leu Ala Ala Gln Gln Thr Tyr
                                                 405                410 aac cac ctg gac atg agt gtg gga gaa gcc ctg agg cag agg aca cta       8465
Asn His Leu Asp Met Ser Val Gly Glu Ala Leu Arg Gln Arg Thr Leu
                415                 420                 425 tgt ctg gag gga gtc ctt tcc tgc cag ccc cac gag agc ttg ggg gaa       8513
Cys Leu Glu Gly Val Leu Ser Cys Gln Pro His Glu Ser Leu Gly Glu
        430                 435                 440 gtg atc gac agg att gct cgg gag cag g taccgtgtgc cctccattca           8561
Val Ile Asp Arg Ile Ala Arg Glu Gln
445                 450 tgcccccaac acatatagcc cagtccttct catgcacggc tccagccatc cctgaacatc     8621
gggcacctgg cctatccttc catttcatga ccaactcctg gtgcccacac tggcctgcac     8681
ctggtcctgt ccatggggcc cttatgccag gggtcactgc caactgatca ccttaggccg     8741
gtcacaccat ccctaactgg tttctaggag acgctctctc cctcagtcat gttgggttgt     8801 ttccctgat tcttggcacc aacctcagta gctgctgtag ccccatggct ctgccccctc      8861
actgaacatt gcggacccac agg ta   cac agg ctg gtg cta gtg gac gag acc    8913
                               Val His Arg Leu Val Leu Val Asp Glu Thr
                                               455                 460 cag cat ctc ttg ggc gtg gtc tcc ctc tcc gac atc ctt cag gca ctg       8961
Gln His Leu Leu Gly Val Val Ser Leu Ser Asp Ile Leu Gln Ala Leu
        465                 470                 475 gtg ctc agc cct gct ggc atc gat gcc ctc ggg gcc tgagaagatc            9007
Val Leu Ser Pro Ala Gly Ile Asp Ala Leu Gly Ala
        480                 485 tgagtcctca atcccaagcc acctgcacac ctggaagcca atgaagggaa ctggagaact     9067
cagccttcat cttcccccac ccccatttgc tgg                                   9100

<210> SEQ ID NO 6
<211> LENGTH: 489
```

<212> TYPE: PRT
<213> ORGANISM: Homo sapiens

<400> SEQUENCE: 6

```
Met Glu Pro Gly Leu Glu His Ala Leu Arg Arg Thr Pro Ser Trp Ser
1               5                   10                  15

Ser Leu Gly Gly Ser Glu His Gln Glu Met Ser Phe Leu Glu Gln Glu
            20                  25                  30

Asn Ser Ser Ser Trp Pro Ser Pro Ala Val Thr Ser Ser Ser Glu Arg
        35                  40                  45

Ile Arg Gly Lys Arg Arg Ala Lys Ala Leu Arg Trp Thr Arg Gln Lys
50                  55                  60

Ser Val Glu Glu Gly Glu Pro Pro Gly Gln Gly Gly Pro Arg Ser
65              70                  75                  80

Arg Pro Ala Ala Glu Ser Thr Gly Leu Glu Ala Thr Phe Pro Lys Thr
                85                  90                  95

Thr Pro Leu Ala Gln Ala Asp Pro Ala Gly Val Gly Thr Pro Pro Thr
            100                 105                 110

Gly Trp Asp Cys Leu Pro Ser Asp Cys Thr Ala Ser Ala Ala Gly Ser
        115                 120                 125

Ser Thr Asp Asp Val Glu Leu Ala Thr Glu Phe Pro Ala Thr Glu Ala
130                 135                 140

Trp Glu Cys Glu Leu Glu Gly Leu Leu Glu Glu Arg Pro Ala Leu Cys
145                 150                 155                 160

Leu Ser Pro Gln Ala Pro Phe Pro Lys Leu Gly Trp Asp Asp Glu Leu
                165                 170                 175

Arg Lys Pro Gly Ala Gln Ile Tyr Met Arg Phe Met Gln Glu His Thr
            180                 185                 190

Cys Tyr Asp Ala Met Ala Thr Ser Ser Lys Leu Val Ile Phe Asp Thr
        195                 200                 205

Met Leu Glu Val Lys Lys Ala Phe Phe Ala Leu Val Ala Asn Gly Val
    210                 215                 220

Arg Ala Ala Pro Leu Trp Asp Ser Lys Lys Gln Ser Phe Val Gly Met
225                 230                 235                 240

Leu Thr Ile Thr Asp Phe Ile Leu Val Leu His Arg Tyr Tyr Arg Ser
                245                 250                 255

Pro Leu Val Gln Ile Tyr Glu Ile Glu Gln His Lys Ile Glu Thr Trp
            260                 265                 270

Arg Gly Ile Tyr Leu Gln Gly Cys Phe Lys Pro Leu Val Ser Ile Ser
        275                 280                 285

Pro Asn Asp Arg Leu Phe Glu Ala Val Tyr Thr Leu Ile Lys Asn Arg
290                 295                 300

Ile His Arg Leu Pro Val Leu Asp Pro Val Ser Gly Asn Val Leu His
305                 310                 315                 320

Ile Leu Thr His Lys Arg Leu Leu Lys Phe Leu His Ile Phe Gly Ser
                325                 330                 335

Leu Leu Pro Arg Pro Ser Phe Leu Tyr Arg Thr Ile Gln Asp Leu Gly
            340                 345                 350

Ile Gly Thr Phe Arg Asp Leu Ala Val Val Leu Glu Thr Ala Pro Ile
        355                 360                 365

Leu Thr Ala Leu Asp Ile Phe Val Asp Arg Arg Val Ser Ala Leu Pro
370                 375                 380

Val Val Asn Glu Cys Gly Gln Val Val Gly Leu Tyr Ser Arg Phe Asp
385                 390                 395                 400
```

Val Ile Asp Leu Ala Ala Gln Gln Thr Tyr Asn His Leu Asp Met Ser
                405                 410                 415

Val Gly Glu Ala Leu Arg Gln Arg Thr Leu Cys Leu Glu Gly Val Leu
            420                 425                 430

Ser Cys Gln Pro His Glu Ser Leu Gly Glu Val Ile Asp Arg Ile Ala
        435                 440                 445

Arg Glu Gln Val His Arg Leu Val Leu Val Asp Glu Thr Gln His Leu
    450                 455                 460

Leu Gly Val Val Ser Leu Ser Asp Ile Leu Gln Ala Leu Val Leu Ser
465                 470                 475                 480

Pro Ala Gly Ile Asp Ala Leu Gly Ala
            485

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
caccatggag cccgagctgg agca                                      24

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gtctcaggcg ctgagggcat c                                         21

<210> SEQ ID NO 9
<211> LENGTH: 33
<212> TYPE: DNA
<213> ORGANISM: Artificial Sequence
<220> FEATURE:
<223> OTHER INFORMATION: Mutated sequence

<400> SEQUENCE: 9
gtggccaacg gtgtgcaggc agctcctctg tgg                            33

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gctgcccagc aaacctacaa c                                         21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
aagatggctt gggtgtgagg ac                                        22

```
<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
tgctcccatt catcagttcc atag                                              24
```